United States Patent [19]

Porte

[11] 4,073,940
[45] Feb. 14, 1978

[54] METHOD FOR TREATING CARDIAC ARHYTHMIA BY ADMINISTRATION OF BASIC ARYLOXYACETAMIDE

[75] Inventor: Laurent Porte, Sanary-sur-Mer, France

[73] Assignee: Centre Europeen de Recherches Pharmacologiques C.E.R.P.H.A., Val-de-Marne, France

[21] Appl. No.: 736,522

[22] Filed: Oct. 28, 1976

[51] Int. Cl.² ........................................... A61K 31/165
[52] U.S. Cl. ..................................................... 424/324
[58] Field of Search ........................................ 424/324

[56] References Cited
U.S. PATENT DOCUMENTS
3,818,021   6/1974   Thuillier et al. ................. 260/295 S Primary Examiner—Albert T. Meyers
Assistant Examiner—Daren M. Stephens
Attorney, Agent, or Firm—Stevens, Davis, Miller & Mosher

[57] ABSTRACT

New method for treating cardiac arhythmia by administering to a patient N-(2,5-diethoxy phenyl)-N-(2-diethylamino ethyl)-4-butoxyphenoxy acetamide or a pharmaceutically acceptable acid addition salt thereof.

3 Claims, No Drawings

METHOD FOR TREATING CARDIAC ARHYTHMIA BY ADMINISTRATION OF BASIC ARYLOXYACETAMIDE

The invention relates to the treatment of cardiac arhythmia. It provides a new method for treating a patient from troubles of cardiac rythm, which comprises administering to the said patient N-(2,5-diethoxy phenyl)-N-(2-diethylaminoethyl)-4-butoxy phenoxy acetamide or a pharmaceutically acceptable acid addition salt thereof. This compound has been described in U.S. Pat. No. 3,818,021 issued June 18, 1974 (example 4 and formula 24 in the tables) and was indicated particularly as a spasmolytic and a cerebral vasodilatator.

Unexpectedly, new researches have shown that this compound is an effective antiarhythmic agent. The invention provides a method for administering this compound in a nontoxic amount sufficient to restore normal cardiac rythm.

The applicant carried out clinical investigation on atrial and ventricular arhythmias with N-(2,5-diethoxy phenyl)-N-(2-diethylamino ethyl)-4-butoxy phenoxy acetamide hydrochloride. In the following examples this compound was administered orally in capsules containing 100 mg of dosage units.

EXAMPLE 1

Subject treated for an atrial flutter, having for 5 months atrial fibrillation; 3 capsules daily for 8 days suppressed the arhythmia.

EXAMPLE 2

Subject with atrial fibrillation; 3 capsules daily for 2 days suppressed the arhythmia.

EXAMPLE 3

Subject with atrial fibrillation; 2 capsules daily stopped the cardiac arhythmia which start again after the suppression of the treatment.

EXAMPLE 4

Subject with atrial fibrillation and bradycardia. The arhythmia is suppressed by 3 capsules daily, the third day.

EXAMPLE 5

Subject with bigeminism. After 15 days, 3 capsules daily, the electrocardiogram is regular, without bigeminism.

The antiarhythmic compositions of this invention are prepared in conventional unit form by incorporating N-(2,5-diethoxy phenyl) N-(2-diethylaminoethyl)-4-butoxyphenoxyacetamide or a salt thereof with a non toxic pharmaceutical carrier according to accepted procedures. The pharmaceutical forms can be for example hard gelatin capsules for oral administration containing from 25 mg to 150 mg of active ingredient, or sterile injectable ampuls for intravenous administration containing from 20 to 50 mg of active ingredient.

Specific examples of dosage forms are as follows:
Ampuls for intravenous administration:

| Ingredients | Quantity |
|---|---|
| N-(2,5-diethoxy phenyl)-N-(2-diethylamino ethyl)-4-butoxy phenoxy acetaide, hydrochloride | 25 mg |
| glucose | 250 mg |
| water for injection : sufficient quantity to | 5 ml |
| Hard gelatin capsules for oral administration : | |
| N-(2,5 diethoxy phenyl)-N-(2-diethylamino ethyl)-4-butoxy phenoxy acetamide, hydrochloride | 100 mg |
| talc | 20 mg |
| magnesium stearate | 5 mg |
| micronized hydrated silica | 1 mg. |

The method, according to the invention, of suppressing cardiac arhythmias comprises administered by oral or intravenous route to a patient the compound of formula I and salts thereof, usually combined with a pharmaceutical carrier, the dosage amount being from 20 to 500 mg of the compound, the daily regimen being from 2 to 5 capsules (during 2 to 5 days) and 2 capsules after, or being from 1 to 4 ampuls.

What I claim:

1. A method for treating a patient for cardiac arhythmia which comprises administering to the said patient N-(2,5-diethoxy phenyl)-N-(2-diethylamino ethyl)-4-butoxy phenoxy acetamide, or a pharmaceutically acceptable acid addition salt thereof, the mode of administration being oral or intravenous and the daily dosage being from 20 mg to about 500 mg of active ingredient.

2. The method of claim 1 in which oral dosage unit is from 50 to 150 mg.

3. The method of claim 1 in which intravenous dosage unit is from 20 to 50 mg.

* * * * *